(12) United States Patent
Rosendahl et al.

(10) Patent No.: US 9,079,154 B2
(45) Date of Patent: Jul. 14, 2015

(54) CATALYST FOR THE EPOXIDATION OF ALKENES

(71) Applicant: BASF SE, Ludwigshafen (DE)

(72) Inventors: Tobias Rosendahl, Mannheim (DE); Torsten Mäurer, Lambsheim (DE); Dirk Hensel, Kaiserslautern (DE); Andreas Lehr, Wachenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/872,506

(22) Filed: Apr. 29, 2013

(65) Prior Publication Data

US 2013/0296587 A1    Nov. 7, 2013

Related U.S. Application Data

(60) Provisional application No. 61/642,473, filed on May 4, 2012.

(51) Int. Cl.
| | |
|---|---|
| *B01J 23/00* | (2006.01) |
| *C07D 301/03* | (2006.01) |
| *B01J 27/02* | (2006.01) |
| *C07D 301/04* | (2006.01) |
| *C07D 301/08* | (2006.01) |
| *B01J 37/08* | (2006.01) |
| *B01J 23/68* | (2006.01) |
| *B01J 35/10* | (2006.01) |
| *B01J 37/00* | (2006.01) |
| *B01J 37/02* | (2006.01) |
| *B01J 37/03* | (2006.01) |
| *B01J 37/06* | (2006.01) |

(52) U.S. Cl.
CPC .............. *B01J 27/02* (2013.01); *B01J 23/685* (2013.01); *B01J 23/686* (2013.01); *B01J 23/688* (2013.01); *B01J 35/109* (2013.01); *B01J 35/1066* (2013.01); *B01J 35/1076* (2013.01); *B01J 37/0036* (2013.01); *B01J 37/0201* (2013.01); *B01J 37/0213* (2013.01); *B01J 37/08* (2013.01); *C07D 301/04* (2013.01); *C07D 301/08* (2013.01); *B01J 37/031* (2013.01); *B01J 37/06* (2013.01)

(58) Field of Classification Search
CPC ........ B01J 23/685; B01J 23/658; B01J 27/02; B01J 37/0213; B01J 37/08; B01J 37/0036; B01J 37/0201; B01J 37/031; B01J 37/06; B01J 35/1066; B01J 35/1076; B01J 35/109; C07D 301/08; C07D 301/04
USPC .................. 502/218, 216, 348, 310; 549/536
See application file for complete search history.

(56) References Cited

U.S. PATENT DOCUMENTS

| | | | |
|---|---|---|---|
| 3,962,136 A | 6/1976 | Nielsen et al. | |
| 4,007,135 A | 2/1977 | Hayden et al. | |
| 4,324,699 A | 4/1982 | Mross et al. | |
| 4,389,338 A | 6/1983 | Mitsuhata et al. | |
| 4,732,918 A | 3/1988 | Lohmueller et al. | |
| 4,774,222 A | 9/1988 | Rashkin | |
| 4,874,739 A * | 10/1989 | Boxhoorn ..................... | 502/218 |
| 5,011,809 A | 4/1991 | Herzog et al. | |
| 2005/0096219 A1 | 5/2005 | Szymanski et al. | |
| 2009/0198076 A1 | 8/2009 | Guckel | |
| 2009/0270640 A1 | 10/2009 | Maurer et al. | |
| 2011/0196162 A1 | 8/2011 | Gitter | |
| 2012/0264951 A1 | 10/2012 | Rosendahl et al. | |
| 2012/0264952 A1 | 10/2012 | Rosendahl et al. | |
| 2012/0264953 A1 | 10/2012 | Rosendahl et al. | |
| 2012/0264954 A1 | 10/2012 | Rosendahl et al. | |

FOREIGN PATENT DOCUMENTS

| | | |
|---|---|---|
| DE | 23 00 512 A1 | 7/1973 |
| DE | 2300512 | 7/1973 |
| DE | 24 54 972 A1 | 6/1975 |
| DE | 25 21 906 A1 | 12/1975 |
| DE | 2454927 A1 | 5/1976 |
| DE | 27 53 359 A1 | 6/1979 |
| DE | 31 50 205 A1 | 8/1982 |
| DE | 33 21 895 A1 | 12/1983 |
| DE | 34 14 717 A1 | 10/1985 |
| DE | 25 60 684 C2 | 10/1989 |
| EP | 0003642 * | 8/1979 |
| EP | 0011356 A1 | 5/1980 |
| EP | 14 457 A2 | 8/1980 |
| EP | 0082609 A1 | 6/1983 |
| EP | 0065237 A1 | 8/1983 |
| EP | 0172665 A2 | 2/1986 |

(Continued)

OTHER PUBLICATIONS

International Search Report for PCT/IB2013/053169, dated Sep. 26, 2013.

(Continued)

*Primary Examiner* — T. Victor Oh

(74) *Attorney, Agent, or Firm* — Drinker Biddle & Reath LLP

(57) ABSTRACT

The present invention relates to a catalyst for preparing alkylene oxides, which is a supported silver catalyst having a novel promoter combination. The present invention further relates to a process for producing the catalyst and the use of the catalyst for the oxidation of alkylenes to alkylene oxides. In addition, the present invention relates to a process for preparing ethylene oxide from ethylene, which comprises the oxidation of ethylene in the presence of the stated catalyst.

20 Claims, No Drawings

(56) References Cited

FOREIGN PATENT DOCUMENTS

| | | |
|---|---|---|
| EP | 0229465 A1 | 7/1987 |
| EP | 0266015 A1 | 5/1988 |
| EP | 0339748 A2 | 11/1989 |
| EP | 0357293 A1 | 3/1990 |
| EP | 384 312 A1 | 8/1990 |
| EP | 0 480 538 A1 | 4/1992 |
| EP | 0496386 A1 | 7/1992 |
| WO | WO-03/072244 A1 | 9/2003 |
| WO | WO-2006133187 A2 | 12/2006 |
| WO | WO-2007/122090 A2 | 11/2007 |
| WO | WO 2010/007011 A1 | 1/2010 |
| WO | WO-2010/123856 A1 | 10/2010 |

OTHER PUBLICATIONS

Özbek et al., "The Mechanism of Ethylene Epoxidation Catalysis," 143 *Catal. Lett.* 131-41 (2013).

International Preliminary Report on Patentability for PCT/IB2013/053169 dated Sep. 17, 2014.

U.S. Appl. No. 13/780,310, filed Sep. 5, 2013, Shishkov et al.

U.S. Appl. No. 13/661,575, filed Oct. 22, 2013, Rosendahl et al.

Ref. No. DIN ISO 9277, May 2003, English price group 10, Sales No. 0410, pp. 1-11.

Ullmann's Encyclopedia of Industrial Chemistry, Fifth, Completely Revised Edition, vol. A10, (1987) "Ethylene Oxide", pp. 117-135.

\* cited by examiner

CATALYST FOR THE EPOXIDATION OF ALKENES

CROSS-REFERENCE TO RELATED APPLICATIONS

This application claims benefit (under 35 USC 119(e)) of U.S. Provisional Application 61/642,473, filed May 4, 2012, which is incorporated by reference.

The present invention relates to a catalyst for preparing alkylene oxides, which is a supported silver catalyst having a novel promoter combination. The present invention further relates to a process for producing the catalyst and the use of the catalyst for the oxidation of alkylenes to alkylene oxides. In addition, the present invention relates to a process for preparing ethylene oxide from ethylene, which comprises the oxidation of ethylene in the presence of the stated catalyst.

Ethylene oxide is an important basic chemical and on an industrial scale is frequently prepared by direct oxidation of ethylene by means of oxygen in the presence of silver-comprising catalysts. Use is frequently made of supported catalysts in which the catalytically active metallic silver has been applied to a support by means of a suitable process. As supports, it is in principle possible to use various porous materials such as activated carbon, titanium dioxide, zirconium dioxide or silicon dioxide or ceramic compositions or mixtures of these materials. In general, alpha-aluminum oxide is used as support.

Apart from silver as active component, these catalysts often comprise promoters for improving the catalytic properties (WO 2007/122090, WO 2010/123856). Examples of promoters are alkali metal compounds and/or alkaline earth metal compounds. Some documents teach the use of transition metals such as cobalt (EP 0 480 538), tungsten or molybdenum. A particularly preferred promoter for influencing the activity and selectivity of catalysts is rhenium. In industry, preference is given to using catalysts comprising rhenium and/or other transition metal promoters in combination with alkali metal compounds and/or alkaline earth metal compounds because of their high selectivity. Selectivity is, for example in the case of the oxidation of ethylene, the molar percentage of ethylene which reacts to form ethylene oxide. The activity of the catalyst is characterized by the ethylene oxide concentration at the reactor outlet under otherwise constant conditions, for example temperature, pressure, gas throughput, amount of catalyst, etc. The higher the ethylene oxide concentration in the reactor output stream, the higher the activity of the catalyst. The lower the temperature required for achieving a particular ethylene oxide concentration, the higher the activity. In order to achieve a high selectivity, the combination of the active metal with the promoters and the composition of the support are usually matched to one another in order to obtain catalysts having very good properties.

The direct oxidation of ethylene to ethylene oxide using supported silver catalysts is described, for example, in DE-A-2300512, DE-A 2521906, EP-A-0014457, DE-A-2454972, EP-A-0172565, EP-A-0357293, EP-A-0266015, EP-A-0011356, EP-A-0085237, DE-A-2560684 and DE-A-2753359.

It is an object of the present invention to provide novel catalysts for the epoxidation of alkenes, which display advantageous activities and/or selectivities.

We have accordingly found novel catalysts in which silver and also the elements molybdenum and tin but not tungsten have been applied as promoters to a support.

The invention accordingly provides a tungsten-free catalyst for the epoxidation of alkenes, which comprises silver, molybdenum and tin applied to a support.

The catalyst of the invention comprises a support. Supports suitable for the purposes of the invention can be produced by processes known from the prior art. Examples are the processes described in US 2009/0198076 A1, WO 2006/133187, WO 03/072244, US 2005/0096219 A1 and EP 0 496 386 B2.

Examples of suitable support materials are aluminum oxide, silicon dioxide, silicon carbide, titanium dioxide, zirconium dioxide and mixtures thereof, with aluminum oxide being preferred. In a preferred embodiment, the present invention accordingly provides a catalyst whose support is an aluminum oxide support.

The term aluminum oxide as used here comprises all conceivable structures such as alpha-, gamma- or theta-aluminum oxide. In a preferred embodiment, the support is an alpha-aluminum oxide support. The present invention accordingly also provides a catalyst in which the support is an alpha-aluminum oxide.

In a further preferred embodiment, the alpha-aluminum oxide has a purity of at least 75%, preferably a purity of at least 80%, more preferably a purity of at least 85%, more preferably a purity of at least 90%, more preferably a purity of at least 98%, more preferably a purity of at least 98.5% and particularly preferably a purity of at least 99%.

The term alpha-aluminum oxide accordingly also comprises alpha-aluminum oxides which comprise further constituents, for example elements selected from the group consisting of zirconium, alkali metals, alkaline earth metals, silicon, zinc, gallium, hafnium, boron, fluorine, copper, nickel, manganese, iron, cerium, titanium, chromium and compounds of these elements and also mixtures of two or more of these elements and/or compounds thereof.

In general, a catalyst support suitable for the purposes of the present invention can be produced by mixing the aluminum oxide with water or another suitable liquid and also a burnout material or a pore former and at least one binder. Suitable pore formers are, for example, cellulose and cellulose derivatives such as methylcellululose, ethylcellulose, carboxymethylcellulose or polyolefins such as polyethylene and polypropylene or natural burnout materials such as ground walnut shells. The pore formers are selected so that they are completely burnt out of the aluminum oxide to form the finished alpha-aluminum oxide support at the furnace temperatures selected for the calcination. Suitable binders or extrusion aids are described, for example, in EP 0 496 386 B2. Mention may be made by way of example of aluminum oxide gels with nitric acid or acetic acid, cellulose, e.g. methylcellulose, ethylcellulose or carboxyethylcellulose or methyl stearate or ethyl stearate, polyolefin oxides, waxes and similar substances.

The paste formed by mixing can be brought to the desired shape by extrusion. To assist the extrusion process, it is possible to use extrusion aids.

The shaped body obtained as described above is, after shaping, usually optionally dried and calcined to give the aluminum oxide support. Calcination is usually carried out at temperatures in the range from 1200° C. to 1600° C. It is usual to wash the aluminum oxide support after calcination in order to remove soluble constituents.

The alpha-aluminum oxide can comprise the further constituents in any suitable form, for example as elements and/or in the form of one or more compounds. If the alpha-aluminum oxide comprises one or more constituents in the form of a compound, it comprises these as, for example, oxide or mixed oxide. Supports which are suitable for the purposes of the invention therefore also include alpha-aluminum oxides comprising at least one further constituent selected from the group consisting of silicon dioxide, sodium oxide, potassium oxide, calcium oxide and magnesium oxide, nickel oxide, gallium oxide, hafnium oxide, copper oxide, iron oxide and mixtures thereof.

As regards the amount of the further constituents, the totality of the further constituents is preferably in the range of less than 25% by weight, more preferably less than 20% by weight, more preferably less than 15% by weight, more preferably less than 10-% by weight, more preferably less than 5% by weight, more preferably less than 2% by weight, more preferably less than 1.5% by weight and particularly preferably less than 1% by weight, based on the total weight of the support.

If the support comprises, for example, alkali metals, it preferably comprises these in a total amount in the range from 10 to 2500 ppm, more preferably in an amount of from 10 to 1000 ppm, more preferably in an amount of from 50 to 850 ppm, based on the total weight of the support and calculated as element. In an embodiment, the support comprises at least one alkali metal selected from the group consisting of sodium and potassium. If the support comprises, for example, sodium, it preferably comprises this in an amount in the range from 10 to 1500 ppm, more preferably in an amount of from 10 to 800 ppm, more preferably in an amount of from 10 to 500 ppm, based on the total weight of the support and calculated as element. If the support comprises, for example, potassium, it preferably comprises this in an amount in the range from 10 to 1000 ppm, more preferably in an amount of from 10 to 500 ppm, more preferably in an amount of from 10 to 300 ppm, based on the total weight of the support and calculated as element. In an embodiment of the invention, the support comprises, for example, sodium in an amount of from 10 to 1500 ppm and potassium in an amount of from 10 to 1000 ppm.

The present invention accordingly also describes a catalyst whose support comprises sodium in an amount of from 10 to 1500 ppm and potassium in an amount of from 10 to 1000 ppm, particularly preferably sodium in an amount of from 10 to 500 ppm and potassium in an amount of from 10 to 300 ppm, based on the total weight of the support and in each case calculated as element.

If the support comprises, for example, alkaline earth metals, it preferably comprises these in a total amount in the range of up to 2500 ppm, for example in the range from 10 to 2500 ppm, more preferably in an amount of from 10 to 1200 ppm, more preferably in an amount of from 10 to 700 ppm, based on the total weight of the support and calculated as element. In an embodiment, the support comprises at least one alkaline earth metal selected from the group consisting of calcium and magnesium. If the support comprises, for example, calcium, it preferably comprises this in an amount in the range from 10 to 1500 ppm, more preferably in an amount of from 10 to 1000 ppm, more preferably in an amount of from 10 to 500 ppm, based on the total weight of the support and calculated as element. If the support comprises, for example, magnesium, it preferably comprises this in an amount in the range from 10 to 800 ppm, more preferably in an amount of from 10 to 500 ppm, more preferably in an amount of from 10 to 250 ppm, based on the total weight of the support and calculated as element.

The present invention accordingly also describes a catalyst whose support comprises magnesium in an amount of from 10 to 800 ppm and calcium in an amount of from 10 to 1500 ppm, in each case based on the total weight of the support and calculated as element. The support particularly preferably comprises, for example, sodium in an amount of from 10 to 1500 ppm, potassium in an amount of from 10 to 1000 ppm, magnesium in an amount of from 10 to 800 ppm, and calcium in an amount of from 10 to 1500 ppm, in each case based on the total weight of the support and calculated as element.

If the support comprises, for example, silicon, it preferably comprises this in an amount in the range from 50 to 10000 ppm, more preferably in an amount of from 50 to 5000 ppm, more preferably in an amount of from 50 to 600 ppm, based on the total weight of the support and calculated as element.

A support which is preferred for the purposes of the present invention is, for example, an alpha-aluminum oxide which has a purity of at least 90% and comprises from 50 to 10000 ppm of silicon, from 10 to 1500 ppm of sodium and from 10 to 2500 ppm of alkaline earth metals in total, in each case calculated as element and based on the total weight of the support. The support preferably comprises calcium and/or magnesium as alkaline earth metal. Particular preference is given to an alpha-aluminum oxide which has a purity of at least 98% by weight and comprises from 50 to 5000 ppm of silicon, from 10 to 800 ppm of sodium and from 10 to 700 ppm of alkaline earth metals in total, in each case calculated as element and based on the total weight of the support.

The support used for the catalyst of the invention preferably has a BET surface area, determined in accordance with the method described in the standard ISO 9277, of from 0.1 to 5 $m^2/g$, more preferably in the range from 0.1 to 2 $m^2/g$, more preferably in the range from 0.5 to 1.5 $m^2/g$, more preferably in the range from 0.6 to 1.3 $m^2/g$ and particularly preferably in the range from 0.6 to 1.0 $m^2/g$.

Furthermore, the supports used for the catalyst of the invention preferably have pores having diameters in the range from 0.1 to 100 μm, with the pore distribution being able to be monomodal or polymodal, for example bimodal, trimodal or tetramodal. The supports preferably have a bimodal pore distribution. The supports more preferably have a bimodal pore distribution having peak maxima in the range from 0.1 to 10 μm and from 15 to 100 μm, preferably in the range from 0.1 to 5 μm and from 17 to 80 μm, more preferably in the range from 0.1 to 3 μm and from 20 to 50 μm, more preferably in the range from 0.1 to 1.5 μm and from 20 to 40 μm. The pore diameters are determined by Hg porosimetry (as described in the standard DIN 66133). The term "bimodal pore distribution having peak maxima in the range from 0.1 to 10 μm and from 15 to 100 μm", as used above, indicates that one of the two peak maxima is in the range from 0.1 to 10 μm and the other peak maximum is in the range from 15 to 100 μm.

The present invention accordingly also describes a catalyst whose support has a bimodal pore distribution, preferably a bimodal pore distribution comprising at least pores having a pore diameter in the range from 0.1 to 15 μm and pores having a pore diameter in the range from 15 to 100 μm, determined by Hg porosimetry.

The geometric shape of the support is generally of minor importance, but the support should advantageously be in the form of particles which allow unhindered diffusion of the reaction gases to a very large part of the outer surface area coated with the catalytically active silver particles and optionally further promoters and internal surface area of the support. The selected geometric shape of the support should ensure a very small pressure drop over the entire reactor length. In a preferred embodiment, the support is used as shaped bodies, for example as extrudate, hollow extrudate, star extrudate, sphere, ring or hollow ring. The support is preferably a shaped body having the geometry of a hollow body. Particular preference is given to cylinders having the following geometries (external diameter×length×internal diameter, in each case reported in mm): 5×5×2, 6×6×3, 7×7×3, 8×8×3, 8×8.5×3, 8×8.5×3.5, 8.5×8×3.5, 8.5×8×3, 9×9×3, 9.5×9×3, 9.5×9×3.5. Each length indicated is subject to tolerances in the region of ±0.5 mm.

According to the invention, it is also possible for the catalyst to be used in the form of crushed catalyst material obtained from one or more of the shaped bodies mentioned.

The water absorption of the support is, for example, in the range from 0.35 ml/g to 0.65 ml/g, preferably in the range from 0.42 ml/g to 0.52 ml/g, determined by vacuum cold-water uptake. The catalyst of the invention comprises silver as active metal. The catalyst can comprise silver in an amount of, for example, from 5 to 35% by weight, in particular from 10 to 30% by weight, preferably in an amount of from 10 to 25% by weight, based on the total weight of the catalyst and calculated as element. The silver is preferably applied in the form of a silver compound, which can be a salt or a silver complex, to the support. The silver compound is preferably applied as a solution, in particular as a solution in water. In order to obtain the silver compound in soluble form, a complexing agent such as ethanolamine, EDTA, 1,3- or 1,2-propanediamine, ethylenediamine and/or an alkali metal oxalate can also be added in an appropriate way to the silver compound, for example silver (I) oxide or silver (I) oxalate and this complexing agent can also simultaneously act as reducing agent. Silver is particularly preferably applied in the form of a silver-amine compound, particularly preferably a silver-ethylenediamine compound.

Furthermore, the catalyst of the invention comprises at least one of the elements molybdenum and tin as promoters. For the purposes of the present invention, a promoter is a constituent of the catalyst by means of which an improvement in one or more catalytic properties, e.g. selectivity, activity, conversion, yield and/or operating life, compared to a catalyst which does not comprise the constituent is achieved. Preference is given to compounds which under the reaction conditions are largely chemically stable and do not catalyze any undesirable reactions. Promoters are usually used in a total amount of from 10 to 3000 ppm and each in an amount of from 5 to 1500 ppm, more preferably each in an amount of from 10 to 1300 ppm and particularly preferably each in an amount of from 50 to 1300 ppm, based on the total weight of the catalyst and calculated as sum of the elements. Promoters are preferably applied in the form of compounds to the support, for example in the form of complexes or in the form of salts, for example in the form of halides, fluorides, bromides or chlorides, or in the form of carboxylates, nitrates, sulfates or sulfides, phosphates, cyanides, hydroxides, carbonates, oxides, oxalates or as salts of heteropolyacids, for example in the form of salts of heteropolyacids of rhenium.

The catalyst of the invention preferably comprises molybdenum in an amount of from 10 to 300 ppm, more preferably in an amount of from 10 to 200 ppm, more preferably in an amount of from 10 to 80 ppm, based on the total weight of the catalyst and calculated as element. Molybdenum is preferably applied as a compound, for example as halide, oxyhalide, oxide, molybdate, permolybdate or as acid, preferably as a compound selected from the group consisting of molybdenum oxide, ammonium heptamolybdate, ammonium orthomolybdate, molybdenum chloride, molybdenum fluoride, molybdenum sulphide and molybdic acid. For the purposes of the invention, molybdenum is particularly preferably applied as molybdic acid ($MoO_3 \cdot H_2O$) to the support.

The catalyst of the invention preferably comprises tin in an amount of from 10 to 600 ppm, more preferably in an amount of from 50 to 400 ppm, more preferably in an amount of from 80 to 250 ppm, based on the total weight of the catalyst and calculated as element. Tin is preferably applied as a compound, for example as halide, hydroxide, oxalate, oxide, stannate or as acid, preferably as a compound selected from the group consisting of tin oxide, tin chloride, tin fluoride, sodium stannate, sodium hexahydroxostannate, stannic acid and tin oxalate. For the purposes of the invention, tin is particularly preferably applied as tin oxalate to the support.

Furthermore, the catalyst of the invention is tungsten-free. For the purposes of the present invention, a tungsten-free catalyst is a catalyst which has a tungsten content of less than 5 mg/kg; tungsten is preferably not detectable analytically. In any case, tungsten compounds are not used in the production of the catalyst.

In a preferred embodiment, the catalyst comprises silver, molybdenum and tin and also at least one further promoter, for example five, four, three or two further promoters or one further promoter. All promoters known in the prior art are conceivable as at least one further promoter. The at least one further promoter is preferably selected from the group consisting of the elements lithium, sodium, potassium, rubidium, cesium, beryllium, magnesium, calcium, strontium, barium, manganese, rhenium, cadmium, chromium, sulfur and mixtures of two or more thereof. The catalyst particularly preferably comprises at least one further promoter selected from the group consisting of the elements rhenium, cesium, lithium, chromium, manganese, sulfur and mixtures of two or more thereof. The catalyst very particularly preferably comprises at least rhenium as further promoter and at least one element selected from the group consisting of cesium, lithium, chromium, manganese, sulfur and mixtures of two or more thereof.

The present invention accordingly also describes a tungsten-free catalyst comprising silver in an amount of from 5 to 35% by weight, based on the total weight of the catalyst, molybdenum and tin and also at least rhenium as further promoter, applied to a support.

If the catalyst comprises, for example, rhenium, it preferably comprises rhenium in an amount of from 50 to 600 ppm, more preferably in an amount of from 100 to 450 ppm, more preferably in an amount of from 150 to 400 ppm, based on the total weight of the catalyst and calculated as element. Rhenium is preferably applied as a compound, for example as halide, oxyhalide, oxide, rhenate, perrhenate or as acid. If rhenium is to be used as promoter, it is preferably applied as a compound selected from the group consisting of ammonium perrhenate, rhenium(III) chloride, rhenium(V) chloride, rhenium(V) fluoride, rhenium(VI) oxide and rhenium (VII) oxide. For the purposes of the invention, rhenium is particularly preferably applied as ammonium perrhenate to the support.

If the catalyst comprises, for example, cesium, it preferably comprises this in an amount of from 20 to 850 ppm, in particular in an amount of from 100 to 600 ppm, based on the total weight of the catalyst and calculated as element. Cesium is preferably applied as cesium compound to the support. Here, any suitable cesium compound can in principle be used. Cesium is preferably applied in the form of cesium hydroxide.

If the catalyst comprises, for example, lithium, it preferably comprises this in an amount of from 10 to 450 ppm, in particular in an amount of from 50 to 300 ppm, based on the total weight of the catalyst and calculated as element. Lithium is preferably applied as lithium compound to the support. Here, any suitable lithium compound can in principle be used. Lithium is preferably applied in the form of lithium nitrate.

It the catalyst comprises, for example, sulfur, it preferably comprises this in an amount of from 5 to 300 ppm, in particular in an amount of from 5 to 150 ppm, based on the total weight of the catalyst and calculated as element. Sulfur is preferably applied as sulfur compound to the support. Here, any suitable sulfur compound can in principle be used. Sulfur is preferably applied in the form of ammonium sulfate.

In a particularly preferred embodiment, the catalyst of the invention comprises rhenium in an amount of from 150 to 450 ppm, cesium in an amount of from 100 to 600 ppm, lithium in an amount of from 50 to 300 ppm and sulfur in an amount of from 5 to 150 ppm.

The promoters, more preferably the promoter compounds, are preferably dissolved in a suitable solvent, preferably in water, before application. The support is then preferably impregnated with the resulting solution comprising one or more of the promoters. If a plurality of promoters are to be added, these can be applied either together or separately to the support in a single impregnation step or in a plurality of impregnation steps. As regards the solution comprising one or more of the promoters, this can be produced in any suitable way. For example, the promoters can be dissolved separately in one solution each and the resulting solutions comprising in each case one promoter can subsequently be used for the impregnation. It is likewise possible to dissolve two or more promoters together in a solution and subsequently use the resulting solution for the impregnation. In addition, it is possible to combine the resulting solutions comprising at least one promoter before impregnation and apply the resulting solution comprising all promoters to the support.

If, for example, at least molybdenum, tin, cesium, lithium, sulfur and rhenium are used as promoters, in a particularly preferred embodiment at least one solution comprising cesium, a further solution comprising molybdenum, a further solution comprising lithium and sulfur, a further solution comprising tin and a further solution comprising rhenium are produced. The solutions are either applied to the support in separate impregnation steps or are combined to form one solution before application and only then used for impregnation. The solutions are preferably applied together, more preferably together with the mixture comprising silver as silver-amine compound, preferably as silver-ethylenediamine compound, to the support.

As regards the application of silver, this can be applied to the support by means of all impregnation and deposition processes of the prior art for producing silver catalysts for the preparation of ethylene oxide, with these processes being able to comprise one or more impregnation and calcination steps. For example, mention may be made of the production processes for silver catalysts disclosed in DE-A 23005112, DE-A 2521906, EPA 0 014 457, EP-A 0 085 237, EP-A 0 0384 312, DE-A 2454927, DE-A 3321895, EP-A 0 229 465, DE-A 3150205, EP-A 0 172 565 and EP-A 0 357 293.

The silver can be applied separately or together with one or more promoters. Preference is given to applying a mixture comprising silver and at least one promoter to the support, for example by impregnation, spraying or mixing processes. The order of application of the promoters and of the silver can generally be chosen at will, i.e. embodiments in which silver and the promoters are applied simultaneously to the support are comprised. Likewise, embodiments in which silver and the promoters are applied in various steps to the support are comprised, with the order of the steps generally being able to be chosen at will. Furthermore, embodiments in which part of the promoters is applied to the support before or after application of the silver and the remaining part is applied simultaneously with silver are comprised. Preference is given to applying silver and the promoters simultaneously to the support.

The invention further provides a process for producing tungsten-free catalysts for the epoxidation of alkenes, which comprises application of silver, molybdenum and tin to a support.

The application can in principle be carried out by any suitable methods, for example by impregnation of the support. The application is particularly preferably effected by vacuum impregnation at room temperature. In vacuum impregnation, the support is preferably firstly treated at a pressure in the range of not more than 500 mbar, more preferably at a pressure of not more than 250 mbar and particularly preferably at a pressure of not more than 50 mbar, and preferably at a temperature in the range from 2° C. to 50° C., more preferably at a temperature in the range from 5° C. to 30° C. and particularly preferably at room temperature. The vacuum treatment is, for example, carried out for a time of at least 1 minute, preferably at least 5 minutes, more preferably for a time in the range from 5 minutes to 120 minutes, in particular in the range from 10 minutes to 45 minutes, particularly preferably in the range from 15 minutes to 30 minutes. After the vacuum treatment, the at least one solution, for example the mixture comprising silver, molybdenum and tin or at least one solution comprising at least one further promoter, preferably the mixture comprising silver, molybdenum and tin and the at least one further promoter, is applied to the support. The solution is preferably dripped on or sprayed on, preferably sprayed on. Application is in this case preferably effected by means of a nozzle. After the application, the support is preferably evacuated further. The evacuation is preferably carried out at a pressure in the range of not more than 500 mbar, more preferably at a pressure of not more than 250 mbar and particularly preferably at a pressure of not more than 50 mbar, and preferably at a temperature in the range from 2° C. to 50° C., more preferably at a temperature in the range from 5° C. to 30° C., and particularly preferably at room temperature. The vacuum treatment is carried out, for example, for a time of at least 1 minute, preferably at least 5 minutes, more preferably for a time in the range from 5 minutes to 120 minutes, in particular in the range from 10 minutes to 45 minutes, particularly preferably in the range from 10 minutes to 20 minutes.

The application of silver, molybdenum, tin and optionally further promoters to a support can be followed by at least one after-treatment step, for example one, two or more drying steps. Drying is usually carried out at temperatures in the range from 2 to 200° C. The after-treatment step is drying by means of vacuum treatment, for example, as described above.

The present invention accordingly also provides a process for producing tungsten-free catalysts for the epoxidation of alkenes, which comprises application of silver, molybdenum and tin to a support and a drying step.

The support material is preferably calcined after the application of silver, molybdenum, tin and optionally further promoters, optionally after a drying step. Calcination is preferably carried out at temperatures in the range from 150 to 750° C., preferably in the range from 200 to 500° C., more preferably in the range from 220 to 350° C., more preferably in the range from 250 to less than 300° C. and particularly preferably in the range from 270 to 295° C., with the calcination time generally being at least 5 minutes or more, for example in the range from 5 minutes to 24 hours or in the range from 10 minutes to 12 hours. The calcination time is particularly preferably in the range from 5 minutes to 3 hours. The calcination can be carried out at a constant temperature. Furthermore, embodiments in which the temperature is altered continuously or discontinuously during the calcination time are comprised.

The calcination can be carried out under any gas atmosphere suitable for this purpose, for example in an inert gas or a mixture of inert gas and from 10 ppm to 21% by volume of oxygen. Inert gases which may be mentioned are, for example, nitrogen, argon, carbon dioxide, helium and mixtures of the abovementioned inert gases. If the calcination is carried out in an inert gas, nitrogen is particularly preferred. In an alternative preferred embodiment, air and/or lean air are/is used.

Furthermore, the calcination is preferably carried out in a muffle furnace, convection oven, in a rotary furnace and/or a belt calcination oven.

The present invention accordingly also provides a process for producing tungsten-free catalysts for the epoxidation of alkenes, which comprise application of silver, molybdenum and tin to a support, optionally a drying step and a calcination, preferably at a temperature in the range from 270 to 295° C.

In a preferred embodiment of the present invention, the support material impregnated with silver, molybdenum and tin obtained by the above-described process, which has a temperature $T_0$, is calcined in a multistage process. This process comprises at least the following steps:

(1) heating the impregnated support material from the temperature $T_0$ to a temperature $T_1$ at a heating rate of at least 30 K/min, preferably in the range from 30 to 80 K/min, more preferably in the range from 40 to 75 K/min;
(2) holding the support material which has been heated to the temperature $T_1$ at a temperature $T_2$, where $T_2$ is preferably in the range from 0.95 $T_1$ to 1.1 $T_1$;
(3) cooling the support material which has been held at the temperature $T_2$ to a temperature $T_3$, where $T_3$ is not more than 60° C.

Should the impregnated support material be obtained at a temperature of greater than $T_0$ in the impregnation, in particular in the particularly preferred one-step impregnation, it is, according to the invention, firstly cooled to the temperature $T_0$.

Temperatures $T_0$ in the range up to 35° C., for example in the range up to 30° C. are conceivable in principle. The temperature $T_0$ is preferably in the range from 5 to 20° C., more preferably in the range from 10 to 15° C.

In preferred embodiments, the temperature $T_0$ is, according to the invention, such that the impregnated support material obtained does not have to be subjected to predrying before it is heated according to the invention at a heating rate of at least 30 K/min in step (1).

The present invention thus preferably provides a process in which the support material impregnated with silver, molybdenum, tin and optionally further promoters obtained by the above-described process is not subjected to a temperature which is greater than 35° C., preferably greater than 30° C., more preferably greater than 25° C. and more preferably greater than 20° C., before being heated at a heating rate of at least 30 K/min.

In step (1) of the calcination process according to the invention, the impregnated support material which has been provided at the temperature To is heated at a heating rate of at least 30 K/min.

Heating rates of up to 150 K/min, for example up to 100 K/min or 80 K/min, are conceivable. The heating rate in step (1) is preferably in the range from 30 to 80 K/min, more preferably in the range from 40 to 75 K/min.

In step (1) of the calcination process according to the invention, the support material is heated from the temperature $T_0$ to the temperature $T_1$.

According to the invention, heating is carried out to temperatures $T_1$ which are suitable for calcination of the impregnated support material. Here, temperatures $T_1$ of up to 350° C., for example up to 340° C. or up to 330° C. or up to 320° C. or up to 310° C. or up to 300° C., are conceivable in principle. Preferred minimum temperatures $T_1$ are in the region of 250° C. Accordingly, temperatures $T_1$ in the range from 250 to 310° C. or in the range from 250 to 300° C. are conceivable. However, it has been found, according to the invention, that it is possible to set calcination temperatures of less than 300° C. The present invention therefore provides the process as described above in which the temperature $T_1$ is less than 300° C., preferably less than or equal to 299° C.

According to the invention, the temperature $T_1$ is preferably in the range from 250 to 295° C., more preferably in the range from 260 to 295° C., more preferably in the range from 270 to 295° C., more preferably in the range from 270 to 290° C., for example in the range from 270 to 285° C., from 275 to 290° C., or from 275 to 285° C.

As concerns the way in which the heating rate according to the invention is achieved, there are in principle no restrictions. Preference is given to the support material present at the temperature $T_0$ being brought into contact with a gas during heating, with further preference being given to heating the support material by means of this gas and the gas thus having a temperature which allows the support material to be heated to the temperature $T_1$.

As regards the chemical composition of the gas which is brought into contact with the support material in order to heat the support material, there are in principle no restrictions. It is thus conceivable for the gas to comprise oxygen, with mention being able to be made by way of example of oxygen contents of the gas of up to 100% by volume or up to 25% by volume. The use of air, for example, is also conceivable. Lower contents of oxygen are also conceivable, with, for example, mixtures of nitrogen and air, e.g. lean air, being conceivable. Mention may be made of oxygen contents of the gas of up to 20% by volume or up to 15% by volume or up to 10% by volume or up to 5% by volume or up to 1% by volume. For the purposes of the present invention, particular preference is given to using an inert gas or a mixture of two or more inert gases, with the oxygen content preferably being less than 10 ppm, more preferably in the range from 5 to 9 ppm, as gas for heating. As inert gases, mention may be made by way of example of nitrogen, carbon dioxide, argon and/or helium. For the purposes of the present invention, nitrogen is particularly preferably used as inert gas.

The present invention accordingly provides the process as described above in which heating in step (1) is carried out by bringing the support material into contact with an inert gas $I_1$.

The present invention preferably provides the process as described above in which heating in step (1) is carried out by bringing the support material into contact with an inert gas $I_1$ which comprises less than 10 ppm, preferably from 5 to 9 ppm, of oxygen.

The present invention more preferably provides the process as described above in which heating in step (1) is carried out by bringing the support material into contact with an inert gas $I_1$, where the inert gas is nitrogen and the inert gas comprises less than 10 ppm, preferably from 5 to 9 ppm, of oxygen.

The expression "inert gas $I_1$ comprising less than 10 ppm, preferably from 5 to 9 ppm, of oxygen" refers here to a gas mixture comprising the inert gas $I_1$ and oxygen, where the oxygen content of less than 10 ppm or from 5 to 9 ppm relates to the oxygen content of the gas mixture and the inert gas $I_1$ can be a mixture of 2 or more inert gases.

For the purposes of the present invention, the gas which is brought into contact with the support material during heating in step (1) is very particularly preferably technical-grade nitrogen, preferably obtained from fractionation of air, which typically comprises nitrogen in an amount of from 99.995 to 99.9999, oxygen in an amount of from 6 to 8 ppm and traces of noble gases.

The temperature of the gas which is brought into contact with the support material during heating is in principle selected so that the heating rates according to the invention can be made possible and the support material can be brought to the temperature $T_1$. The gas with which the support material is brought into contact during heating in step (1) preferably has a temperature in the range from $T_1$ to $1.1\ T_1$, more preferably in the range from $T_1$ to $1.07\ T_1$, more preferably in the range from $T_1$ to $1.05\ T_1$.

The contacting of the support material with the gas in step (1) can in principle be carried out in any desired way as long as it is ensured that the heating rate according to the invention is achieved for the support material. In this regard, particular preference is given to bringing the support material into contact with a stream of the gas, preferably a stream of the inert gas $I_1$, i.e. passing the gas through the support material. Here, the volume flow of the gas is basically selected so that the heating rate according to the invention is achieved. In particular, the volume flow of the gas is selected so that the heating rate according to the invention is achieved by the combination of the temperature and the volume flow of the gas which is brought into contact with the support material. The volume flow is particularly preferably in the range from 2500 to 5000 m$^3$/h, in particular in the range from 3200 to 4500 m$^3$/h.

In a preferred embodiment, the present invention provides the process as described above in which an inert gas $I_1$, preferably nitrogen, is passed through the support material to be heated up in step (1), where $I_1$ preferably comprises less than 10 ppm, more preferably from 5 to 9 ppm, of oxygen, $I_1$ preferably has a temperature in the range from $T_1$ to $1.1\ T_1$ and $I_1$ preferably flows through the support material at a volume flow in the range from 2500 to 5000 m$^3$/h, more preferably from 3200 to 4500 m$^3$/h.

During heating of the support material as per step (1), the heating rate can be constant or can vary, as long as it is ensured that the overall heating rate calculated from the temperature difference $(T_1-T_0)$ divided by the total time required for heating is at least 30 K/min, preferably in the range from 30 to 80 K/min, more preferably in the range from 30 to 75 K/min, more preferably in the range from 30 to 70 K/min. The heating rate during the total heating operation is preferably at least 30 K/min, more preferably in the range from 30 to 80 K/min, more preferably in the range from 30 to 75 K/min, more preferably in the range from 30 to 70 K/min.

Ranges which are possible according to the invention for the heating rate are, for example, from 35 to 80 K/min or from 40 to 75 K/min or from 40 to 70 K/min or from 45 to 70 K/min or from 50 to 70 K/min or from 55 to 70 K/min or from 60 to 70 K/min or from 65 to 70 K/min.

In step (2) of the calcination process according to the invention, the support material which has been heated to the temperature $T_1$ is, after heating, preferably directly after heating, maintained at a temperature $T_2$ which is suitable for the purposes of the calcination according to the invention. Preference is here given to temperatures $T_2$ in the region of the temperature $T_1$. Particular preference is given to temperatures $T_2$ in the range from 0.95 to $1.1\ T_1$, for example in the range from 0.95 to $1.05\ T_1$, from 0.96 to $1.04\ T_1$, from 0.97 to $1.03\ T_1$, from 0.98 to $1.02\ T_1$ or from 0.99 to $1.01\ T_1$. The temperature $T_2$ is preferably selected so as to be less than 300° C., preferably less than or equal to 299° C.

Holding of the support material at the temperature $T_2$ also comprises embodiments in which the value of $T_2$ is not constant during the hold time but instead varies within the above-described limits. The present invention thus also comprises, inter alia, embodiments in which the holding is carried out at two or more different temperatures which are within the above-described limits $T_2$.

The time for which the support material is held at the temperature $T_2$ is in principle not subject to any restrictions. For the purposes of the present invention, preference is given to the support being held at the temperature $T_2$ for a time in the range from 1 to 15 minutes, preferably from 2 to 10 minutes, more preferably from 3 to 5 minutes, in step (2).

As regards the way in which the holding according to the invention in step (2) is achieved, there are in principle no restrictions. During holding at the temperature $T_2$, the support material is preferably brought into contact with a gas which is at a temperature which allows the support material to be maintained at the temperature $T_2$.

As regards the chemical composition of the gas which is brought into contact with the support material in order to hold the support material at the temperature $T_2$, there are in principle no restrictions. It is thus conceivable, for instance, for the gas to comprise oxygen, with, for example, oxygen contents of the gas of up to 100% by volume or up to 25% by volume being possible. The use of air, for example, is also conceivable. Lower contents of oxygen are also conceivable, with, for example, mixtures of nitrogen and air, e.g. lean air, being conceivable. Mention may be made of oxygen contents of the gas of up to 20% by volume or up to 15% by volume or up to 10% by volume or up to 5% by volume or up to 1% by volume. For the purposes of the present invention, particular preference is given to using an inert gas or a mixture of two or more inert gases, in which the oxygen content is preferably less than 10 ppm, more preferably in the range from 5 to 9 ppm, as gas for holding at the temperature $T_2$. As inert gases, mention may be made by way of example of nitrogen, carbon dioxide, argon and helium. Particular preference is given to using nitrogen as inert gas for the purposes of the present invention.

The present invention accordingly provides the process as described above in which the holding as per step (2) is carried out by bringing the support material into contact with an inert gas $I_2$.

The present invention preferably provides the process as described above in which the holding in step (2) is carried out by bringing the support material into contact with an inert gas $I_2$ comprising less than 10 ppm, preferably from 5 to 9 ppm, of oxygen.

The present invention more preferably provides the process as described above in which the holding in step (2) is carried out by bringing the support material into contact with an inert gas $I_2$, where the inert gas is nitrogen and the inert gas comprises less than 10 ppm, preferably from 5 to 9 ppm, of oxygen.

The expression "inert gas $I_2$ comprising less than 10 ppm, preferably from 5 to 9 ppm, of oxygen" refers here to a gas mixture comprising the inert gas $I_2$ and oxygen, where the oxygen content of less than 10 ppm or from 5 to 9 ppm relates to the oxygen content of the gas mixture and the inert gas $I_2$ can be a mixture of 2 or more inert gases.

For the purposes of the present invention, the gas with which the support material is brought into contact during the holding in step (2) is very particularly preferably technical-grade nitrogen, preferably obtained from fractionation of air, which typically comprises nitrogen in amounts of from 99.995 to 99.9999% by volume, oxygen in amounts of from 6 to 8 ppm and traces of noble gases.

The temperature of the gas with which the support material is brought into contact during holding in step (2) is basically selected so that the hold temperature according to the invention can be made possible. The gas with which the support material is brought into contact during holding in step (2) preferably has a temperature in the range from $T_2$ to 1.1 $T_2$, more preferably in the range from $T_2$ to 1.07 $T_2$, more preferably in the range from $T_2$ to 1.05 $T_2$, for example in the range from $T_2$ to 1.04 $T_2$ or in the range from $T_2$ to 1.03 $T_2$ or in the range from $T_2$ to 1.02 $T_2$ or in the range from $T_2$ to 1.01 $T_2$.

The contacting of the support material with the gas in step (2) can in principle be carried out in any desired way as long as it is ensured that the holding according to the invention of the support material at the temperature $T_2$ is achieved. In this regard, particular preference is given to the support material being brought into contact with a stream of the gas, preferably with a stream of the inert gas $I_2$, i.e. the gas being passed through the support material. Here, the volume flow of the gas is basically selected so that the holding according to the invention of the support material at the temperature $T_2$ is achieved. In particular, the volume flow of the gas is selected so that the holding according to the invention of the support at the temperature $T_2$ is achieved by the combination of the temperature and the volume flow of the gas which is brought into contact with the support material. The volume flow is particularly preferably in the range from 1000 to 3000 m³/h, more preferably from 1500 to 2000 m³/h.

In a preferred embodiment, the present invention provides the process as described above in which an inert gas $I_2$, preferably nitrogen, is passed through the support material to be held at the temperature $T_2$ in step (2), where $I_2$ preferably comprises less than 10 ppm, more preferably from 5 to 9 ppm, of oxygen, $I_2$ preferably has a temperature in the range from $T_2$ to 1.05 $T_2$ and $I_2$ preferably flows through the support at a volume flow in the range from 1000 to 3000 m³/h, more preferably from 1500 to 2000 m³/h.

It is preferred, but not necessary, that the inert gas $I_1$ is used as inert gas $I_2$ for the purposes of the present invention, with, as described above, the volume flow of $I_2$ being able to be different from the volume flow of $I_1$ and/or the temperature of $I_2$ being able to be different from the temperature of $I_1$.

In step (3) of the calcination process according to the invention, the support material which has been held at the temperature $T_2$ is cooled after holding, preferably directly after holding, to a temperature $T_3$. As regards the value of $T_3$, there are in principle no particular restrictions. For the purposes of the present invention, temperatures $T_3$ of not more than 60° C. are preferred.

As regards the way in which the cooling according to the invention in step (3) is achieved, there are in principle no restrictions. During cooling to the temperature $T_3$, the support material is preferably brought into contact with a gas which has a temperature which allows the support material to be cooled to the temperature $T_3$.

As regards the chemical composition of the gas which is brought into contact with the support material in order to cool the support material to the temperature $T_3$, there are in principle no restrictions. It is thus conceivable, for instance, for an inert gas as is used, for example, in steps (1) or (2) to be used as gas. For the purposes of the present invention, particular preference is given to using a gas having an oxygen content of at least 5% by volume, preferably at least 10% by volume, more preferably at least 15% by volume, more preferably at least 20% by volume, as gas for cooling to the temperature $T_3$. In particular, air is used according to the invention for effecting cooling in step (3).

In the process of the invention, the support material is preferably cooled at a cooling rate in the range from 30 to 80 K/min, preferably in the range from 40 to 60 K/min, more preferably in the range from 45 to 55 K/min, in step (3).

The calcined and cooled support material obtained in this way can either be used as catalyst immediately after step (3) or it can be stored in a suitable way.

As regards the apparatus used for the above-described calcination process, there are essentially no restrictions as long as it is ensured that the heating according to the invention in step (1), preferably also the holding according to the invention in step (2), preferably also the cooling according to the invention in step (3) can be carried out as described above. According to the invention, preference is given to embodiments in which at least the heating in step (1), preferably the heating in step (1) and holding in step (2) and also the cooling in step (3), is/are carried out continuously. With particular preference the process of the invention is carried out in a belt calciner in respect of step (1), preferably at least in respect of steps (1) and (2).

As regards the time at which the promoters are applied, they can also be applied after the above-described calcination. As well, it is possible to apply the promoters together with the silver compound to the support.

Accordingly, the invention comprises embodiments in which the at least one further promoter, that is to say, for example, five different further promoters, four different further promoters, three different further promoters, two different further promoters or one further promoter are applied to the support and the support which has been treated in this way is only subsequently calcined as described above to give a catalyst according to the invention.

The present invention further provides a process for preparing ethylene oxide from ethylene, which comprises oxidation of ethylene in the presence of a tungsten-free catalyst for the epoxidation of alkenes, which comprises silver, molybdenum and tin applied to a support.

In addition, the present invention also provides for the use of a tungsten-free catalyst comprising silver, molybdenum and tin applied to a support for the epoxidation of alkenes.

According to the invention, the epoxidation can be carried out by all processes known to those skilled in the art. Here, it is possible to use all reactors which can be used in the ethylene oxide production processes of the prior art, for example externally cooled shell-and-tube reactors (cf. Ullmann's Encyclopedia of Industrial Chemistry, 5th edition, vol. A-10, pp. 117-135, 123-125, VCH-Verlagsgesellschaft, Weinheim 1987), or reactors having a loose catalyst bed and cooling tubes, for example the reactors described in DE-A 3414717, EP 0082609 and EP-A 0339748. The epoxidation is preferably carried out in at least one tube reactor, preferably in a shell-and-tube reactor. The catalyst of the invention can be used either alone or in admixture with other catalysts in a combined or structured catalyst bed.

The preparation of ethylene oxide from ethylene and oxygen can, according to the invention, be carried out under conventional reaction conditions as are described, for example, in DE 25 21 906 A1, EP 0 014 457 A2, DE 2 300 512 A1, EP 0 172 565 A2, DE 24 54 972 A1, EP 0 357 293 A1, EP 0 266 015 A1, EP 0 085 237 A1, EP 0 082 609 A1 and EP 0 339 748 A2. Inert gases such as nitrogen or gases such as water vapour and methane which are inert under the reaction conditions and optionally reaction moderators, for example halides, hydrocarbons such as ethyl chloride, vinyl chloride or 1,2-dichloroethane, can additionally be mixed into the reaction gas comprising ethylene and molecular oxygen. The oxygen content of the reaction gas is advantageously in a range in which no explosive gas mixtures are present. A suitable composition of the reaction gas for preparing ethylene oxide can comprise, for example, an amount of ethylene in the range from 10 to 80% by volume, preferably from 20 to 60% by volume, more preferably from 25 to 50% by volume and particularly preferably in the range from 30 to 40% by volume, based on the total volume of the reaction gas. The oxygen content of the reaction gas is advantageously in the range of not more than 10% by volume, preferably not more than 9% by volume, more preferably not more than 8% by volume and very particularly preferably not more than 7% by volume, based on the total volume of the reaction gas.

The reaction gas preferably comprises a chlorine-comprising reactor moderator such as ethyl chloride, methyl chloride, vinyl chloride or dichloroethane in an amount of from 0 to 15 ppm, preferably in an amount of from 0.1 to 8 ppm. The remainder of the reaction gas generally comprises hydrocarbons such as methane or else inert gases such as nitrogen. In addition, the reaction gas can also comprise other materials such as water vapor, carbon dioxide or noble gases.

The above-described constituents of the reaction mixture can optionally comprise small amounts of impurities. Ethylene can, for example, be used in any purity which is suitable for the epoxidation according to the invention. Suitable purities include, but are not limited to, polymer-grade ethylene, which typically has a purity of at least 99%, and chemical-grade ethylene, which has a lower purity of typically below 95%. The impurities typically comprise mainly ethane, propane and/or propene.

The epoxidation is usually carried out at elevated temperature. Preference is given to temperatures in the range from 150 to 350° C., more preferably in the range from 180 to 300° C., more preferably in the range from 190 to 280° C. and particularly preferably in the range from 200 to 280° C. The present invention accordingly also provides a process as described above in which the oxidation takes place at a temperature in the range from 180 to 300° C., preferably in the range from 200 to 280° C.

The oxidation is preferably carried out at pressures in the range from 5 bar to 30 bar. The oxidation is more preferably carried out at a pressure in the range from 5 bar to 25 bar, preferably at a pressure in the range from 10 bar to 20 bar and in particular in the range from 14 bar to 20 bar. The present invention accordingly also provides a process as described above in which the oxidation is carried out at a pressure in the range from 14 bar to 20 bar.

The oxidation is preferably carried out in a continuous process. If the reaction is carried out continuously, use is made of a GHSV (gas hourly space velocity) which is, as a function of the type of reactor selected, for example of the size/cross-sectional area of the reactor, the shape and size of the catalyst, preferably in the range from 800 to 10000/h, preferably in the range from 2000 to 6000/h, more preferably in the range from 2500 to 5000/h, where the figures are based on the volume of the catalyst.

The preparation of ethylene oxide from ethylene and oxygen can advantageously be carried out in a circulation process. Here, the reaction mixture is circulated through the reactor with the newly formed ethylene oxide and the by-products formed in the reaction being removed from the product gas stream after each pass and the product stream being, after being supplemented with the required amounts of ethylene, oxygen and reaction moderators, fed into the reactor again. The separation of the ethylene oxide from the product gas stream and its work-up can be carried out by the conventional methods of the prior art (cf. Ullmann's Encyclopedia of Industrial Chemistry, 5th edition, vol. A-10, pp. 117-135, 123-125, VCH-Verlagsgesellschaft, Weinheim 1987).

The present invention is illustrated below with the aid of examples.

1. General Method for Producing Catalysts According to the Invention 1.1 Aluminum Oxide Support Used A bimodal alpha-aluminum oxide support having a hollow ring geometry and the properties shown in table 1 was used.

TABLE 1

| Support used | |
|---|---|
| | Support A |
| Ring geometry (external diameter × length × internal diameter) [mm] | 7.91 × 8.41 × 2.62 |
| BET [$m^2$/g] | 0.82 |
| Water absorption [ml/g] | 0.444 |
| Hg porosimetry Peak maxima [μm] | 1.09, 53.2 |
| Ca [ppm] | 300 |
| Fe [ppm] | 200 |
| K [ppm] | 300 |
| Mg [ppm] | 100 |
| Na [ppm] | 400 |
| Si [ppm] | 600 |

1.2 Production of the Silver Complex Solution 550 g of silver nitrate were dissolved in 1.5 l of water at 40° C. with stirring. 402.62 g of potassium hydroxide solution (47.8%) were mixed with 1.29 l of water. 216.31 g of oxalic acid were subsequently added to the potassium hydroxide solution and completely dissolved, and the solution was heated to 40° C. The potassium oxalate solution was subsequently added to the silver nitrate solution (40° C.) over a period of about 45 minutes (volume flow=about 33 ml/min) by means of a metering pump. After the addition was complete, the resulting solution was stirred at 40° C. for another 1 hour. The precipitated silver oxalate was filtered off and the filtercake obtained was washed with 1 liter portions of water (total of about 10 l) until it was free of potassium and nitrate (determined by means of conductivity measurement on the washings; for the present purposes, potassium- and nitrate-free means a conductivity of <40 μS/cm). The water was removed as completely as possible from the filtercake and the residual moisture content of the filtercake was determined. 620 g of silver oxalate having a water content of 20.80% were obtained.

306 g of ethylenediamine were cooled to about 10° C. in an ice bath and 245 g of water were added in small portions. After the addition of water was complete, 484.7 g of the resulting (still moist) silver oxalate were added in small portions over a period of about 30 minutes. The mixture was stirred overnight at room temperature and the residue was subsequently centrifuged off. The Ag content of the remaining clear solution was determined refractometrically and the density was determined by means of a 10 ml measuring cylinder.

The solution comprised 29.35% by weight of silver, calculated as element, and had a density of 1.536 g/ml.

1.3 Production of the Cobalt or Palladium Complex Solution 12 g of water were cooled to 8° C. by means of an ice/water mixture and 10 g of ethylenediamine were slowly added in portions. 12.7 g of palladium acetate (45.9-48.4% of Pd) or 10.0 g of cobalt acetate (about 33% of Co) were then added slowly in such a way that the temperature did not exceed 20° C.

1.4 Production of the Tin Oxalate Solution

The desired amount of tin oxalate was weighed out and mixed with four parts of distilled water and one part of $H_2O_2$ (30% strength). The reaction mixture was stirred at room temperature until a clear solution had been formed.

1.5 General Method for Production of the Solution Comprising Silver and Promoters The silver complex solution produced as per method 1.2 was placed in a reaction vessel. An aqueous solution comprising lithium and sulfur (lithium nitrate and $(NH_4)_2SO_4$), an aqueous solution comprising cesium (CsOH), an aqueous solution comprising cesium (CsOH) and tungsten ($H_2WO_4$), an aqueous palladium-ethylenediamine complex solution, an aqueous cobalt-ethylenediamine complex solution, an aqueous solution comprising tin (tin oxalate, $SnC_2O_4$), an aqueous solution comprising molybdenum (molybdic acid, $H_2MoO_4$) and/or an aqueous solution comprising rhenium (ammonium perrhenate) were optionally added thereto and the solution was stirred for 5 minutes. The solutions and amounts thereof used for the particular catalyst are shown in detail in the examples under item 2.

1.6 Application of the Solution to the Support

The desired amount of the support A (see table 1) was placed in a rotary evaporator and evacuated. The vacuum was 50 mbar. The support was preevacuated for about 10 minutes.

The solution obtained as per method 1.5 was added dropwise to the support over a period of 15 minutes and reduced pressure and the impregnated support was subsequently rotated under reduced pressure for a further 15 minutes. The support was then left in the apparatus at room temperature and atmospheric pressure for 1 hour and mixed gently every 15 minutes.

1.7 Calcination of the Impregnated Support

The impregnated support was treated in a convection oven (from HORO, model 129 ALV-SP, serial no.: 53270) for 13 minutes at 283° C. under 8.3 $m^3$ of $N_2$ per hour at a heating rate of 40 K/min, a heating time of 360 s and a hold time at 283° C. of 420 s. Cooling to room temperature was carried out over a period of 420 s.

1.8 Production of Crushed Catalyst Material

The catalyst rings obtained were roughly broken up in a porcelain dish by means of a mortar. The comminuted material was subsequently comminuted to the desired particle size fraction (500-900 µm) by means of a sieving machine (from Fritsch) and 2 balls made of sintered alumina. Very hard rings were completely comminuted by means of the mortar and then sieved.

1.9 Epoxidation

The epoxidation was carried out in an experimental reactor comprising a vertical reaction tube made of stainless steel and having an internal diameter of 6 mm and a length of 2200 mm. The reaction tube, which was provided with a jacket, was heated by means of hot oil at a temperature T which flowed through the jacket. To a very good approximation, the temperature of the oil corresponds to the temperature in the reaction tube and thus the reaction temperature.

For the epoxidation, the catalyst was used in the form of crushed catalyst material (particle size fraction 500-900 µm). The reaction tube was filled, from the bottom upward, to a height of 212 mm with inert steatite balls (from 1.0 to 1.6 mm), above this to a height of 1100 mm with 38.2 g of crushed catalyst material, particle size from 0.5 to 0.9 mm, and above this to a height of 707 mm with inert steatite balls (from 1.0 to 1.6 mm). The feed gas entered the reactor from the top and exited again at the lower end after passing through the catalyst bed.

The feed gas comprised 35% by volume of ethylene, 7% by volume of oxygen, 1% by volume of $CO_2$, EC moderation. At the beginning, 2.0 ppm of EC (ethylene chloride) were used for start-up. Depending on the catalyst and performance, the EC concentration was increased every 24 h to a maximum of 8 ppm. The remainder of the feed gas comprised methane. The experiments were carried out at a pressure of 15 bar and a gas hourly space velocity (GHSV) of 4750 1/h and a space-time yield of 250 kg of EO/($m^3$cat×h).

The reaction temperature was regulated to give the prescribed ethylene oxide offgas concentration of 2.7%. To optimize the catalyst in respect of selectivity and conversion, from 2.2 to 4.0 ppm of ethylene chloride were added as moderator to the feed gas.

The gas leaving the reactor was analyzed by means of on-line MS. The selectivity was determined from the analytical results.

The results are summarized in table 2. This shows performance values in the stable operating state with optimal EC moderation after a running-in phase of >100 hours of catalyst operating time.

2. Catalysts Produced:

2.1 Catalyst 1 (Comparative Example)

300 g of the support A was converted according to the general methods 1.2 to 1.7 into the corresponding catalyst.

The following amounts were used in production of the solution as per general method 1.5:

190.25 g of silver complex solution (28.83% of Ag)

2.3698 g of a solution comprising 2.85% of lithium and 0.21% of sulfur 3.5593 g of a solution comprising 2.00% of tungsten and 4.00% of cesium 3.2991 g of a solution comprising 4.1% of rhenium The catalyst produced comprises 15.4% by weight of silver, tungsten in an amount of 200 ppm by weight, cesium in an amount of 400 ppm by weight, lithium in an amount of 190 ppm by weight, sulfur in an amount of 14 ppm by weight and rhenium in an amount of 380 ppm. The catalyst obtained was subsequently tested in accordance with general method 1.9. The result is shown in table 2.

2.2 Catalyst 2 (Comparative Example)

119.9 g of the support A was converted according to the general methods 1.2 to 1.7 into the corresponding catalyst.

The following amounts were used in production of the solution as per general method 1.5:

75.64 g silver complex solution (29.14% of Ag)

0.95 g of a solution comprising 2.85% of lithium and 0.21% of sulfur 1.4241 g of a solution comprising 4.00% of cesium 1.3210 g of a solution comprising 4.1% of rhenium 0.0681 g of water The catalyst produced comprises 15.5% by weight of silver, cesium in an amount of 400 ppm by weight, lithium in an amount of 190 ppm by weight, sulfur in an amount of 14 ppm by weight and rhenium in an amount of 380 ppm.

The catalyst obtained was subsequently tested in accordance with general method 1.9. The result is shown in table 2.

2.3 Catalyst 3 (According to the Invention)

120.2 g of the support A were converted according to general methods 1.2 to 1.7 into the corresponding catalyst.

The following amounts were used in the production of the solution as per general method 1.5:
  73.63 g of silver complex solution (29.14% of Ag)
  0.9458 g of a solution comprising 2.85% of lithium and 0.21% of sulfur
  1.4182 g of a solution comprising 4.00% of cesium
  0.3576 g of a solution comprising 2.00% of molybdenum
  1.0632 g of a solution comprising 2.00% of tin
  1.3136 g of a solution comprising 4.1% of rhenium The catalyst produced comprises 15.2% by weight of silver, cesium in an amount of 400 ppm by weight, lithium in an amount of 190 ppm by weight, sulfur in an amount of 14 ppm by weight, molybdenum in an amount of 50 ppm, tin in an amount of 150 ppm and rhenium in an amount of 380 ppm.

The catalyst obtained was subsequently tested in accordance with general method 1.9. The result is shown in table 2.

2.4 Catalyst 4 (Comparative Example)

119.9 g of the support A were converted according to general methods 1.2 to 1.7 into the corresponding catalyst.

The following amounts were used in the production of the solution as per general method 1.5:
  71.83 g of silver complex solution (29.24% of Ag)
  0.9439 g of a solution comprising 2.85% of lithium and 0.21% of sulfur
  1.4125 g of a solution comprising 4.00% of cesium
  0.3551 g of a solution comprising 2.00% of molybdenum
  1.3101 g of a solution comprising 4.1% of rhenium
  2.5033 g of water The catalyst produced comprises 14.9% by weight of silver, cesium in an amount of 400 ppm by weight, lithium in an amount of 190 ppm by weight, sulfur in an amount of 14 ppm by weight, molybdenum in an amount of 50 ppm and rhenium in an amount of 380 ppm.

The catalyst obtained was subsequently tested in accordance with general method 1.9. The result is shown in table 2.

2.5 Catalyst 5 (Comparative Example)

120.0 g of the support A were converted according to general methods 1.2 to 1.7 into the corresponding catalyst.

The following amounts were used in the production of the solution as per general method 1.5:
  71.90 g of silver complex solution (29.24% of Ag)
  0.9439 g of a solution comprising 2.85% of lithium and 0.21% of sulfur
  1.4149 g of a solution comprising 4.00% of cesium
  1.0622 g of a solution comprising 2.00% of tin
  1.3121 g of a solution comprising 4.1% of rhenium
  1.7943 g of water The catalyst produced comprises 14.9% by weight of silver, cesium in an amount of 400 ppm by weight, lithium in an amount of 190 ppm by weight, sulfur in an amount of 14 ppm by weight, tin in an amount of 150 ppm and rhenium in an amount of 380 ppm.

The catalyst obtained was subsequently tested in accordance with general method 1.9. The result is shown in table 2.

2.6 Catalyst 6 (Comparative Example)

120.1 g of the support A were converted according to general methods 1.2 to 1.7 into the corresponding catalyst.

The following amounts were used in the production of the solution as per general method 1.5:
  74.16 g of silver complex solution (29.55% of Ag)
  0.9490 g of a solution comprising 2.85% of lithium and 0.21% of sulfur
  1.4256 g of a solution comprising 4.00% of cesium and 2.00% of tungsten
  0.3558 g of a solution comprising 2.00% of molybdenum
  1.0683 g of a solution comprising 2.00% of tin
  1.3191 g of a solution comprising 4.1% of rhenium The catalyst produced comprises 15.3% by weight of silver, cesium in an amount of 400 ppm by weight, lithium in an amount of 190 ppm by weight, sulfur in an amount of 14 ppm by weight, tungsten in an amount of 200 ppm, molybdenum in an amount of 50 ppm, tin in an amount of 150 ppm and rhenium in an amount of 380 ppm.

The catalyst obtained was subsequently tested in accordance with general method 1.9. The result is shown in table 2.

2.7 Catalyst 7 (Comparative Example)

120.1 g of the support A were converted according to general methods 1.2 to 1.7 into the corresponding catalyst.

The following amounts were used in the production of the solution as per general method 1.5:
  75.17 g of silver complex solution (29.35% of Ag)
  0.9506 g of a solution comprising 2.85% of lithium and 0.21% of sulfur
  1.4247 g of a solution comprising 4.00% of cesium
  0.2410 g of a solution comprising 9.00% of cobalt
  0.0701 g of a solution comprising 10.6% of palladium
  1.3220 g of a solution comprising 4.1% of rhenium
  0.4253 g of water The catalyst produced comprises 15.5% by weight of silver, cesium in an amount of 400 ppm by weight, lithium in an amount of 190 ppm by weight, sulfur in an amount of 14 ppm by weight, palladium in an amount of 50 ppm, cobalt in an amount of 150 ppm, and rhenium in an amount of 380 ppm.

The catalyst obtained was subsequently tested in accordance with general method 1.9. The result is shown in table 2.

2.8 Catalyst 8 (Comparative Example)

120.1 g of the support A were converted according to general methods 1.2 to 1.7 into the corresponding catalyst.

The following amounts were used in the production of the solution as per general method 1.5:
  75.19 g of silver complex solution (29.35% of Ag)
  0.9502 g of a solution comprising 2.85% of lithium and 0.21% of sulfur
  1.4270 g of a solution comprising 4.00% of cesium and 2.00% of tungsten
  0.2428 g of a solution comprising 9.00% of cobalt
  0.0693 g of a solution comprising 10.6% of palladium
  1.3199 g of a solution comprising 4.1% of rhenium
  0.4134 g of water The catalyst produced comprises 15.5% by weight of silver, cesium in an amount of 400 ppm by weight, tungsten in an amount of 200 ppm, lithium in an amount of 190 ppm by weight, sulfur in an amount of 14 ppm by weight, palladium in an amount of 50 ppm, cobalt in an amount of 150 ppm and rhenium in an amount of 380 ppm.

The catalyst obtained was subsequently tested in accordance with general method 1.9. The result is shown in table 2.

2.9 Catalyst 9 (Comparative Example)

120.2 g of the support A was converted according to general methods 1.2 to 1.7 into the corresponding catalyst.

The following amounts were used in the production of the solution as per general method 1.5:
  75.23 g of silver complex solution (29.35% of Ag)
  0.9505 g of a solution comprising 2.85% of lithium and 0.21% of sulfur
  1.4260 g of a solution comprising 4.00% of cesium
  0.2408 g of a solution comprising 9.00% of cobalt
  0.3582 g of a solution comprising 2.00% of molybdenum
  1.3222 g of a solution comprising 4.1% of rhenium
  0.1344 g of water The catalyst produced comprises 15.5% by weight of silver, cesium in an amount of 400 ppm by weight, lithium in an amount of 190 ppm by weight, sulfur in an amount of 14 ppm by weight, cobalt in an amount of 150 ppm, molybdenum in an amount of 50 ppm and rhenium in an amount of 380 ppm.

The catalyst obtained was subsequently tested in accordance with general method 1.9. The result is shown in table 2.

2.10 Catalyst 10 (Comparative Example)

120.2 g of the support A were converted according to general methods 1.2 to 1.7 into the corresponding catalyst.

The following amounts were used in the production of the solution as per general method 1.5:

74.38 g of silver complex solution (29.35% of Ag)
0.9496 g of a solution comprising 2.85% of lithium and 0.21% of sulfur
1.4263 g of a solution comprising 4.00% of cesium
0.2388 g of a solution comprising 9.00% of cobalt
1.0707 g of a solution comprising 2.00% of tin
1.3101 g of a solution comprising 4.1% of rhenium The catalyst produced comprises 15.5% by weight of silver, cesium in an amount of 400 ppm by weight, lithium in an amount of 190 ppm by weight, sulfur in an amount of 14 ppm by weight, cobalt in an amount of 150 ppm, tin in an amount of 150 ppm and rhenium in an amount of 380 ppm.

The catalyst obtained was subsequently tested in accordance with general method 1.9. The result is shown in Table 2.

The catalysis results show that the catalyst 3 according to the invention displays the best combination of activity and high selectivity. Under the experimental parameters selected, a catalyst which requires a temperature of over 245° C. to achieve the desired ethylene oxide offgas concentration of 2.7% is not suitable for achieving the normally required operating life of about 1 year.

TABLE 2

Comparison of the catalysis results

| Cat. No. | Support | Composition [ppm] | Selectivity [%] | Temperature [° C.] |
|---|---|---|---|---|
| 1 | A | 200 W, standard | 90.2 | 242.8 |
| 2 | A | 0 W, 0 Mo, 0 Sn | 86.7 | 237.6 |
| 3 | A | 0 W, 50 Mo, 150 Sn | 90.5 | 240.3 |
| 4 | A | 0 W, 50 Mo, 0 Sn | 90.2 | 247.8 |
| 5 | A | 0 W, 0 Mo, 150 Sn | 81.9 | 222.6 |
| 6 | A | 200 W, 50 Mo, 150 Sn | 90.8 | 248.3 |
| 7 | A | 0 W, 50 Pd, 150 Co | 83.7 | 236.0 |
| 8 | A | 200 W, 50 Pd, 150 Co | 86.1 | 242.0 |
| 9 | A | 0 W, 50 Mo, 150 Co | 88.3 | 242.0 |
| 10 | A | 0 W, 150 Sn, 150 Co | 84.5 | 243.1 |

The invention claimed is:

1. A tungsten-free catalyst for the epoxidation of alkenes, which comprises silver, and molybdenum, tin, and lithium as a promoters, all of which are applied to a support.

2. The catalyst according to claim 1, wherein the support is an aluminum oxide support.

3. The catalyst according to claim 2, wherein the aluminum oxide has a purity of at least 85%.

4. The catalyst according to claim 1, wherein the support has a bimodal pore distribution.

5. The catalyst according to claim 3, wherein the support has a bimodal pore distribution comprising at least pores having pore diameters in the range from 0.1 to 10 μm and pores having pore diameters in the range from 15 to 100 μm.

6. The catalyst according to claim 1, wherein the silver is present in an amount of from 5 to 35% by weight, based on the total weight of the catalyst and calculated as element.

7. The catalyst according to claim 6, wherein the molybdenum is present in an amount of from 10 to 300 ppm and the tin is present in an amount of from 10 to 600 ppm, based on the total weight of the catalyst and calculated as element.

8. The catalyst according to claim 7, further comprising an additional promoter selected from the group consisting of rhenium, sulfur, cesium, chromium, manganese or mixtures of two and more thereof.

9. The catalyst according to claim 7, further comprising rhenium as an additional promoter present in an amount of from 50 to 600 ppm, based on the total weight of the catalyst and calculated as element.

10. A process for producing tungsten-free catalysts for the epoxidation of alkenes, which comprises applying silver, and molybdenum, tin, and lithium, as a promoters, to a support.

11. The process according to claim 10, which comprises calcination at a temperature in the range from 270 to 295° C.

12. A process for preparing ethylene oxide from ethylene, which comprises oxidation of ethylene in the presence of the catalyst according to claim 1.

13. A process for the epoxidation of alkenes which comprises utilizing the catalyst according to claim 1.

14. The catalyst according to claim 8, wherein the promoter comprises cesium and the cesium is present in an amount of from 100 to 600 ppm, based on the total weight of the catalyst and calculated as element.

15. The catalyst according to claim 1 wherein the selectivity to ethylene oxide is at least 90.5% as measured at a catalytic activity with offgas concentration of ethylene oxide of 2.7%.

16. The catalyst according to claim 15, wherein the selectivity value of the catalyst is measured at an operating temperature of less than 245° C.

17. The process according to claim 12, wherein the selectivity to ethylene oxide is at least 90.5% as measured at a catalytic activity with offgas concentration of ethylene oxide of 2.7%.

18. The process according to claim 17, wherein the catalyst is maintained at an operating temperature of less than 245° C.

19. A tungsten-free catalyst for converting ethylene to ethylene oxide, the catalyst comprising
10 to 25% by weight silver,
10 to 80 ppm molybdenum,
80 to 250 ppm tin, and
50 to 300 ppm lithium, each of which based on the total weight of the catalyst and calculated as element, and all of which are supported on an alumina support.

20. The catalyst according to claim 19, wherein the support has a BET surface area in a range from 0.5 to 1.5 m²/g, determined in accordance with standard ISO 9277, and the support has a bimodal pore distribution having peak maxima in the range from 0.1 to 3 μm and from 20 to 50 μm, determined by Hg porosimetry in accordance with standard DIN 66133.

* * * * *